(12) United States Patent
Lesartre et al.

(10) Patent No.: US 10,452,567 B2
(45) Date of Patent: Oct. 22, 2019

(54) NON-VOLATILE MEMORY TO STORE RESETTABLE DATA

(71) Applicant: HEWLETT-PACKARD DEVELOPMENT COMPANY, L.P., Houston, TX (US)

(72) Inventors: Gregg B. Lesartre, Ft. Collins, CO (US); Andrew Hana, Bristol (GB); Russ W. Herrell, Ft. Collins, CO (US); Gregory Trezise, Wells (GB)

(73) Assignee: Hewlett Packard Enterprise Development LP, Houston, TX (US)

( * ) Notice: Subject to any disclaimer, the term of this patent is extended or adjusted under 35 U.S.C. 154(b) by 461 days.

(21) Appl. No.: 14/785,749

(22) PCT Filed: Apr. 29, 2013

(86) PCT No.: PCT/US2013/038591
§ 371 (c)(1),
(2) Date: Oct. 20, 2015

(87) PCT Pub. No.: WO2014/178814
PCT Pub. Date: Nov. 6, 2014

(65) Prior Publication Data
US 2016/0077979 A1    Mar. 17, 2016

(51) Int. Cl.
*G06F 3/06* (2006.01)
*G06F 12/14* (2006.01)
(Continued)

(52) U.S. Cl.
CPC ......... *G06F 12/1466* (2013.01); *A61B 17/72* (2013.01); *A61B 17/744* (2013.01);
(Continued)

(58) Field of Classification Search
CPC ...... G06F 3/0622; G06F 3/0637; G06F 3/062; G06F 3/0979; G06F 12/14; G06F 12/44;
(Continued)

(56) References Cited

U.S. PATENT DOCUMENTS

| 4,812,841 A * | 3/1989 | Chen | G07C 9/00142 340/5.27 |
| 4,970,504 A * | 11/1990 | Chen | G07C 9/00142 340/5.26 |

(Continued)

FOREIGN PATENT DOCUMENTS

| TW | 201106195 A | 2/2011 |
| TW | 201245962 A | 11/2012 |

OTHER PUBLICATIONS

International Search Report Written Opinion; PCT/US2014/038591; dated Nov. 29, 2016; 13 pages.
(Continued)

Primary Examiner — Larry T Mackall
(74) Attorney, Agent, or Firm — Michael A. Dryja

(57) ABSTRACT

A non-volatile memory (NVM) is to store data and a first password. The first password is to protect the data. A controller is to selectively enable interaction with the data based on authenticating the first password against a second password. A temporary region is to store the second password. The second password is discarded in response to a status change of the apparatus. The data, the first password, and the second password are resettable by the controller in response to a reset request to bypass the first password, such that the apparatus is restorable to an unused state without authenticating the first password.

14 Claims, 5 Drawing Sheets

(51) Int. Cl.
*A61B 17/72* (2006.01)
*A61B 17/74* (2006.01)

(52) U.S. Cl.
CPC .......... *G06F 3/0622* (2013.01); *G06F 3/0637* (2013.01); *G06F 3/0679* (2013.01); *A61B 17/7283* (2013.01); *G06F 2212/1052* (2013.01)

(58) Field of Classification Search
CPC ............. G06F 2212/1052; A61B 17/72; A61B 17/7283; A61F 17/749
USPC ......... 711/152, 164, 166; 713/161, 171, 184
See application file for complete search history.

(56) References Cited

U.S. PATENT DOCUMENTS

| | | | |
|---|---|---|---|
| 5,206,905 A | 4/1993 | Lee et al. | |
| 5,402,492 A * | 3/1995 | Goodman | G06F 21/31 713/166 |
| 5,715,523 A * | 2/1998 | Reynolds | H04B 1/38 455/343.6 |
| 5,892,906 A * | 4/1999 | Chou | G06F 21/31 713/2 |
| 6,012,145 A | 1/2000 | Mathers et al. | |
| 6,012,146 A * | 1/2000 | Liebenow | G06F 21/80 726/17 |
| 6,338,114 B1 * | 1/2002 | Paulsen | G06F 3/0619 711/112 |
| 7,054,990 B1 | 5/2006 | Tamura et al. | |
| 7,913,049 B2 | 3/2011 | Norman | |
| 8,060,670 B2 | 11/2011 | Yu et al. | |
| 8,219,824 B2 | 7/2012 | Chang | |
| 8,819,810 B1 * | 8/2014 | Liu | G06F 21/31 726/18 |
| 2002/0006060 A1 | 1/2002 | Ikeda | |
| 2003/0212871 A1 | 11/2003 | Suzuki et al. | |
| 2005/0228721 A1 | 10/2005 | Hofmann | |
| 2005/0246765 A1 * | 11/2005 | Utsumi | G06F 21/80 726/5 |
| 2006/0004974 A1 | 1/2006 | Lin et al. | |
| 2006/0242425 A1 | 10/2006 | Ishida | |
| 2007/0136523 A1 * | 6/2007 | Bonella | G06F 9/4401 711/113 |
| 2007/0234073 A1 | 10/2007 | Cromer | |
| 2007/0294497 A1 | 12/2007 | Chen | |
| 2008/0263676 A1 | 10/2008 | Mo | |
| 2009/0036096 A1 * | 2/2009 | Ibrahim | H04L 63/083 455/411 |
| 2009/0113155 A1 | 4/2009 | Beals | |
| 2009/0164744 A1 | 6/2009 | Norman | |
| 2009/0204777 A1 * | 8/2009 | Norman | G06F 12/1433 711/163 |
| 2010/0296651 A1 | 11/2010 | Tkacik | |
| 2011/0067460 A1 * | 3/2011 | Niwa | G06F 21/79 70/58 |
| 2011/0154478 A1 * | 6/2011 | Chew | G06F 21/88 726/16 |
| 2012/0210115 A1 * | 8/2012 | Park | H04L 9/3242 713/2 |
| 2013/0013921 A1 * | 1/2013 | Bhathena | H04L 9/0825 713/168 |
| 2013/0212368 A1 * | 8/2013 | Peng | G06F 9/4406 713/2 |
| 2013/0276146 A1 * | 10/2013 | Gilani | H04L 63/10 726/29 |
| 2014/0337946 A1 * | 11/2014 | Jancula | G06F 21/46 726/6 |
| 2015/0095563 A1 * | 4/2015 | Royer, Jr. | G06F 3/06 711/105 |
| 2015/0312233 A1 * | 10/2015 | Graham, III | H04L 9/006 713/171 |

OTHER PUBLICATIONS

Krypto Security Features, Krypto Security, Micron Technology, Inc., Available at: <http://www.micron.com/products/nor-flash/nor-security-overview/krypto-security-technologies>, 2013 (3 pages).

* cited by examiner

NON-VOLATILE MEMORY TO STORE RESETTABLE DATA

BACKGROUND

A computer system may use a memory module, such as a dynamic random-access memory (DRAM) dual in-line memory module (DIMM), to serve as high speed system memory. Such memory modules may be based on volatile memory devices. Volatile memory devices may not retain the contents of their memory when system power is removed (e.g., upon power-down or reset, or when the volatile memory devices are removed from a system). Thus, volatile memory modules may provide a level of security due to the volatility of the memory contents. For example, there is little chance of recovering memory contents by removing the memory module from one motherboard and inserting it into another in an attempt to read its contents. However, volatile memory modules impose other drawbacks, such as a need for a boot-up process to initialize and re-load contents into the memory after a reset or power up.

BRIEF DESCRIPTION OF THE DRAWINGS/FIGURES

DETAILED DESCRIPTION

Non-volatile memory devices may be used as system memory, enabling benefits such as retention of memory contents to enable instant start-up when system power is provided (i.e., bypassing a lengthy boot-up procedure and/or need to reload memory contents at boot-up or reset). The non-volatile nature of such memory systems may enable contents of the non-volatile memory to be accessible when removed from a system, e.g., by a third-party attacker removing the memory and inserting it in another system in an attempt to access user/program data.

Examples provided herein may provide protection for non-volatile memory devices, such as password authentication and/or encryption on the memory device for data access. Techniques may provide protection while minimizing affects to latency, power needs, die area, and/or complexity of the memory devices. Furthermore, examples enable changing a password associated with protecting the memory device, to allow redefinition of access privileges to the memory device, as well as the option to return the device to an unused ('unclaimed') state for redeployment. Thus, examples may address dynamically changing use cases, e.g., for use with storage and/or servers that get redeployed on a routine basis at a data center. Contents of the memory device also may be read out and migrated to an alternate device (e.g., at a different location) without compromising the data security. For example, a service technician or other administrator, without prior knowledge about the memory devices, may migrate data without needing to know access passwords for the memory devices.

Figure 1:
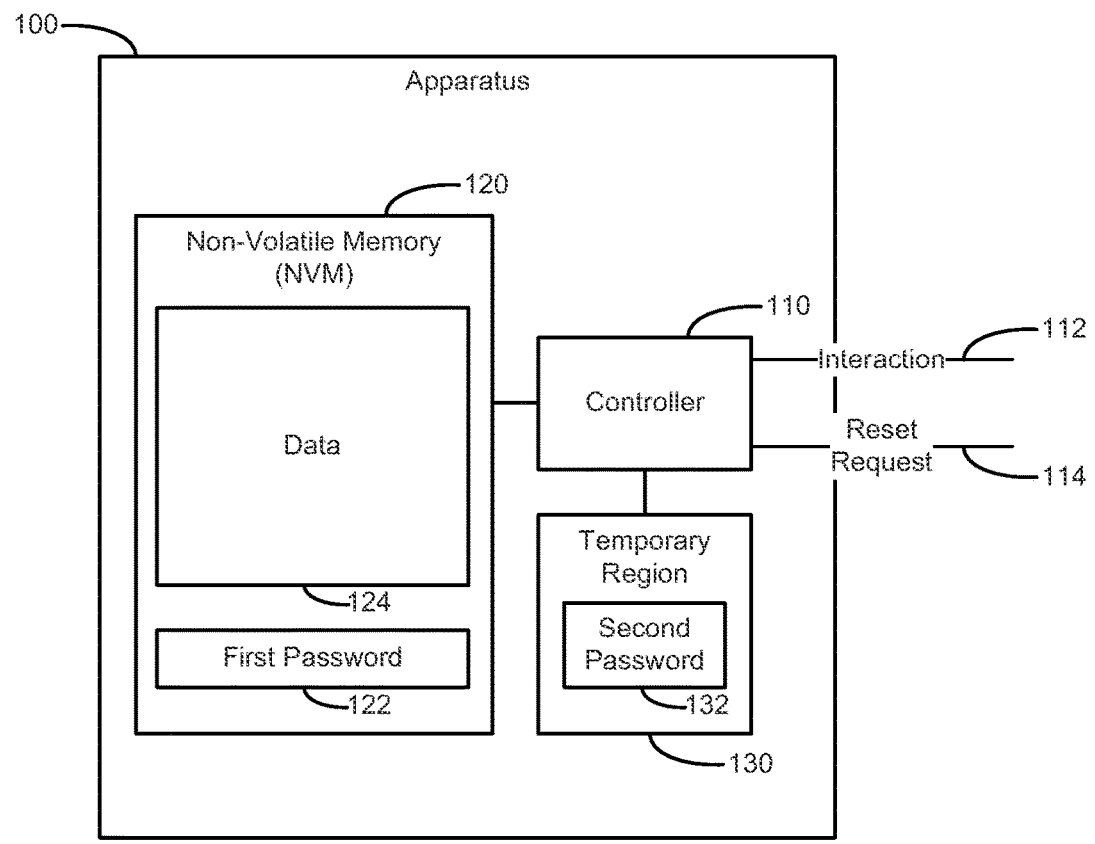
FIG. 1 is a block diagram of an apparatus including non-volatile memory according to an example.

FIG. 1 is a block diagram of an apparatus 100 including non-volatile memory (NVM) 120 according to an example. The NVM includes first password 122 and data 124. The Apparatus 100 also includes controller 110 and temporary region 130. The controller 110 is associated with interaction 112 and reset request 114. The temporary region includes a second password 132.

The apparatus 100 may be usable as a non-volatile system memory (e.g., providing high-speed random-access responsiveness for interaction 112), in contrast to slower storage-based memory such as a hard drive. The apparatus 100 also may include a temporary (e.g., volatile) aspect, based on the temporary region 130 and/or controller 110. Examples of apparatus 100 may provide access checking for, and control over, the data 124, such that apparatus 100 may be contained within a memory module (e.g., DRAM DIMM). For example, a password-based locking mechanism as shown in FIG. 1 may be contained inside a die that contains the NVM cells. In alternate examples, various components of apparatus 100 may be located across a computing system, such as the controller 110 being separate from the NVM 120 and/or temporary region 130 (e.g., via a separate memory controller and/or processor, coupled to a memory module over a bus).

The NVM 120 may include, e.g., an array of memory structures to store the data 124 and first password 122. NVM 120 may be based on technologies such as memristor, phase change memory, resistive RAM storage, flash memory, and other non-volatile technologies to provide high speed random access functionality (e.g., suitable for use as computer system memory). The NVM 120 may include a region allocated to store mode information about operation of the apparatus 100, as well as volatile logic and/or storage (e.g., a portion of the NVM 120 may serve as temporary region 130). Mode information may be a field of mode bits that define how the apparatus 100 is to operate, based on various modes of operation. The allocated NVM 120 may provide a location to store first password 122, to authenticate access to the data 124 stored in the apparatus 100.

The controller 110 may include logic to selectively control access to the NVM 120 (e.g., to the data 124). For example, the controller 110 may allow access to the data 124 if the second password 132 matches the first password 122. Alternatively, the controller 110 may enable resetting the data 124 without password authentication, based on reset request 114. Controller 110 may be implemented as gate-based logic (e.g., as an AND gate), a field-programmable gate array (FPGA), an application-specific integrated circuit (ASIC), or other implementation, that may, e.g., selectively AND output of the NVM 120 with a zero (ground), e.g., to selectively zero out data as desired based on the results of authentication. The controller 110 may include registers and other logic mapped to an in-band control path (indicated as interaction 112 in FIG. 1, and which may include address, data, and/or control signals). In alternate examples, the controller 110 may communicate using a secondary path such as a sideband control associated with a memory module. The secondary communication path may be used in addition to and/or as an alternative to a main in-band data path. For example, controller 110 may interact based on a physical presence pin or other pin(s), such as repurposed existing pins via a strapping option during reset. A strapping option enables a pin, which normally serves one purpose during operation, to be given a separate purpose on reset. Thus, when the apparatus 100 powers up, the controller 110 may sample a control, address, and/or data signal, and latch the state of such signals for use as an input for control operations for a particular mode. A side-band communications channel may enable apparatus 100 to communicate with a memory controller (not shown in FIG. 1), enabling the memory controller to determine a type of memory system of the apparatus 100, and lock or unlock access to the data 124 and other aspects of the memory system of apparatus 100. Local checking and/or an in-band control path may provide access to general operations through normal address data control signals, e.g., to write particular memory locations and set up access control for checking subsequent transactions for enabling data access. Using an out-of-band technique may provide a form of safeguard against, e.g., data access by a rogue process on a system central processing unit (CPU) that uses in-band access to place the apparatus 100 into password reset mode for an attack. Out-of-band techniques may be used to increase security, as a mode that the apparatus 100 may be put in, e.g., when coming out of reset before initializing an application or an operating system (OS) software.

The temporary region 130 may be a non-volatile one-time programmable memory (e.g., a 256-bit allocated portion of NVM 120) to store the second password 132. The temporary region 130 may be temporary (e.g., volatile) in the sense that, when accessed and provided with the second password 132 to be compared with the first password 122 in NVM 120, the temporary region 130 enables the second password 132 to be cleared, e.g., when power is removed or other reset/power cycle occurs. Volatile memory may provide such functionality, and non-volatile memory also may be used by resetting it upon reset of the apparatus 100. The temporary region 130 enables the second password 132 and/or other contents of the temporary region 130 to be non-persistent across resets, power cycles, power loss, and other situations, regardless of whether volatile or non-volatile storage is used.

The temporary region 130 also may be controlled to prevent unauthorized access. For example, access may be prevented until the temporary region 130 (and associated second password) has been written after a system reset that resets a valid bit or other indicator. Such an indicator may be periodically reset even while in use. For example, the apparatus 100 may run a refresh cycle (e.g., when refreshing system memory DIMMs) to reset a validity indicator and force an update for ownership and password renewal.

The temporary region 130 may be allocated by address range as a set of memory that is to be treated as non-persistent. A block of memory may be declared to be non-persistent memory, and a device associated with apparatus 100 (e.g., a host computing system in which apparatus 100 resides) may handle clearing of the declared non-persistent memory as needed, e.g., in response to a reset, power loss, and/or power cycle of the device. Thus, the temporary region 130 may be handled within apparatus 100, below a system OS level, and the system OS does not need to keep track of the persistent memory contents in terms of what needs to be erased every reboot. For example, apparatus 100 may use a set of flags and/or other mode bits to indicate that an allocated memory portion corresponds to the temporary region 130 to be treated as non-persistent memory. The flags/mode bits may indicate that the temporary region 130 has been reset and the second password 132 has not been written, such that the second password 132 is needed before granting access to data 124, or that the data 124 will be cleared. The controller 110 may check status of such flags/mode bits upon power up, reset, or other events (e.g., events that follow a reset), thereby ensuring enough time to clear out a block of memory.

In an example, upon power up, the controller 110 may reset temporary region 130 to a null value and write the second password 132 to the temporary region 130. The controller 110 may use the second password 132 to authenticate the first password 122, before granting access to read the contents of the NVM 120. The controller 110 may return all zeros if the second password 132 does not match the first password 122. Following loss of power (e.g., upon power up and/or reset), the temporary region 130 may be cleared (e.g., by using a volatile memory), and the controller 110 may request that the temporary region 130 be written with the second password 130 to be authenticated against the first password 122 before data accesses may be granted.

Thus, apparatus 100 may perform differently depending on its usage, e.g., whether the apparatus 100 is first being used, during a power-down, or during a power-up. For example, on first use, the apparatus 100 (e.g., a memory module) may not include a first password 122 in the NVM 120. For example, a one-time programmable (OTP) area of the NVM 120 corresponding to storage of a first password 122 may be blank and ready to be programmed. The apparatus 100 memory module may be installed into a computer system as system memory. A basic input/output system (BIOS) of the computer system may start up and determine that the OTP is blank, and prompt for a secure first password 122 that is then programmed into the OTP of the NVM 120. The act of programming the first password 122 may be noted by the controller 110, which is to prevent access to the data 124 and first password 122 until authentication via the second password 132. The controller 110 may allow reads of the data 124 from the NVM 120 out to a memory controller of the computing system.

On power-down, an example apparatus 100 may cause the temporary region 130 to lose all information (including second password 132). For example, temporary region 130 (as well as control and/or gating logic of controller 110) may be based on volatile memory that loses its contents on removal of power. However, the NVM 120 may retain its memory contents, including the first password 122 (e.g., in an OTP area of NVM 120) and data 124, e.g., a memory-array.

On power-up, the controller 110 may gate-off output of the NVM 120, such that output is zero/ground and no reads of the memory system are enabled (output 0). Controller 110 may communicate (e.g., via interaction 112) that the first password 122 (e.g., in the OTP) has been programmed, and that authentication is needed (prompt for entry of the second password 132). Such communication may be visible, e.g., to a BIOS of the computing system hosting the apparatus 100. The controller may thereby lock access to the NVM 120 until the correct second password 132 is received (e.g., such that second password 132 authenticates with the first password 122), upon which the controller 110 may unlock the NVM 120 and allow access to data 124, first password 122, and/or other contents of NVM 120.

Additional features and implementations may be used in examples of apparatus 100. The controller 110 may enable the apparatus 100 to operate according to various modes, e.g., based on mode bits or other indicators that the controller 110 may monitor. A configuration mode may provide for free access to the data 124, where no password is needed. The configuration mode may be used, e.g., before data 124 is written into the NVM 120, such that the apparatus 100 is in a 'claimable' state where a computing system, interfacing with the apparatus 100, could 'claim' the apparatus 100 by assigning the first password 122 and toggling a configuration mode bit to exit the configuration mode. An 'unclaimed' device may be indicated by, e.g., having all zeros as a default first password 122, in addition or as an alternative to using a configuration mode bit. Once the first password 122 is set, the controller 110 may prevent other control and/or data operations until authenticating the first password 122 (e.g., based on the correct second password 132 being entered and/or present).

Upon authentication, e.g., once the matching second password 132 has been provided, the controller 110 may allow the first password 122 in the NVM 120, along with indicators such as configuration bits in the NVM 120, to be written to new values (including clearing of the data 124 and/or the first password 122). Placing the apparatus 100 in a writable state enables the apparatus 100 to be assigned to a different user, virtual machine, and so on. A system interfacing with apparatus 100 may clear the first password 122 so that the apparatus 100 can be redeployed, placing the apparatus 100 in an 'unclaimed' state. The controller 110 may expect to clear the NVM 120 by writing the data locations of the NVM 120 to scrub its contents before clearing, and/or as a condition of clearing, the first password 122.

The apparatus 100 may have a configuration mode, so that the first password 122 may be restricted to being cleared by putting the apparatus 100 in the configuration mode to clear data 124 and first password 122. The controller 110 may write zeros to locations in the apparatus 100 in a prescribed order, then setting the apparatus 100 into an 'unclaimed' (e.g., no password) mode. When in the configuration mode to clear data and password, the controller 110 may force zeros into every data location, and track the order of such writes to guarantee that all locations are zeroed. The controller 110 may ensure that after the proper sequence of commands and write operations are completed, then the first password 122 and/or second password 132 may be cleared and the device returned to the 'unclaimed' state (e.g., for redeployment).

Clearing memory contents may involve control logic associated with address, data, and control blocks that drive the array of NVM 120. Such a block of control in the data path (shown in FIG. 1 as interaction 112 and reset request 114) associated with controller 110 enables shorting memory writes to ground and driving zeros into the NVM 120 array. Such clearing may be carried out by putting the apparatus 100 into a reset password mode, which prevents data access until every location in the memory is cleared.

The apparatus 100 may be operated in a recovery mode (e.g., in response to a reset request 114), to allow recovery, e.g., if the stored first password 122 is lost. The apparatus 100 may be cleared and the first password 122 (and/or second password 132) reset to zeros, e.g., by a similar sequence of commands and writes (which may involve the added assertion of a special side-band signal). Thus, if the apparatus 100 is physically in hand, it may be redeployed without knowledge of the currently stored first password 122 (e.g., including any stored/active key(s)). However, the contents of the apparatus 100 are destroyed in the process of restoring the apparatus 100 to an unclaimed/redeployable state.

Thus, examples of apparatus 100 may have the ability to set the first password 122 and compare it to a temporary second password 132 received after the apparatus 100 is powered up and reset. The first password 122 is treated as non-volatile, and the second password 132 may be treated as active and needing to be downloaded to the temporary region 130 to enable the apparatus 100 for use. Furthermore, examples of apparatus 100 have the ability to reset the first password 122 (e.g., change the first password 122 to a different first password 122), and clear the first password 122 in a manner that can guarantee clearing the NVM 120. Thus, examples enable zeroing out the stored first password 122, even if the currently stored first password 122 is unknown. Accordingly, examples of apparatus 100 are reusable and redeployable, without needing to know the first password 122.

Examples may provide a number of variations of these techniques. For example, the region of NVM 120 for the first password 122 (e.g., an OTP area) may receive and store a number of different password entries, to allow multiple users to unlock a respective portion of the memory system, based on each of their respective different first passwords 122. In an example, the memory system may track/count a number of failed/incorrect password attempts and store this in non-volatile memory. Once a pre-determined threshold/limit has been reached, the memory system may be disabled (e.g., pending being cleared and redeployed, or permanently disabled). In an example, on each power-up, a limited number of password attempts may be allowed before the memory system must be power-cycled, imposing a power-cycle time delay, thereby limiting the viability of a brute-force attack. In an example, the apparatus 100 may use a public-private key system, so that the first password 122 to unlock the memory system does not need to be transmitted un-encrypted (e.g., via a side-band communications channel), and a separate 'safe' public key may be transmitted, keeping the private first password 122 secure.

Thus, many variations and extensions may be used to augment the mechanism of recovering apparatus 100 to an unclaimed (redeployable) state if the first password 122 is lost. As set forth above, an implementation may allow several first passwords 122, with each used to control access to a portion of the NVM 120 (e.g., as defined by a configuration field associated with the NVM 120). In this way, apparatus 100 may control access to different data fields in NVM 120 (e.g., different contexts protected by different passwords), while running operations for processes associated with the contexts. The apparatus 100 may clear the second password 132 of the temporary region 130 before switching context to another process. Additionally, separate passwords may be supported for read and/or write access to the NVM 120. For example, a first password 122 may be required for writes, whereas read-only access (or other types of access) may be granted without needing to authenticate a first password 122.

Examples of apparatus 100 may grant independent access to different portions of the NVM 120, by separate users having independent security access, based on the second password 132 that is received responsive to a transaction request. If the received second password 132 does not match a corresponding one of the stored first passwords 122 for that memory address, the controller 110 may provide null data, or data may be dropped (e.g., for a write). Such a mechanism may prevent separate users from accessing each other's data. Alternatively, separate volatile storage registers may be provided for multiple second passwords 132, each written by the user assigned a password identification (ID) that identifies a corresponding password storage register in the temporary region 130. The password ID may be included in each data access, to apply the correct second password 132 to the access.

Another example technique may be DRAM compatible, based on accessing the apparatus 100 through certain addresses on that DRAM apparatus 100 for certain DRAM control functions, to put apparatus 100 in a mode that does not allow reset of the first password 122 and/or second password 132, or zeroing out of the NVM 120. However, such a mode may support, e.g., removing the apparatus 100 component from an interfacing computing system, and interfacing the apparatus 100 into a separate dedicated 'reset' system. The reset system may enable the apparatus 100 to be reset to an unclaimed/redeployable state, whereas reset may be prevented when deployed to a non-reset system.

Figure 2:
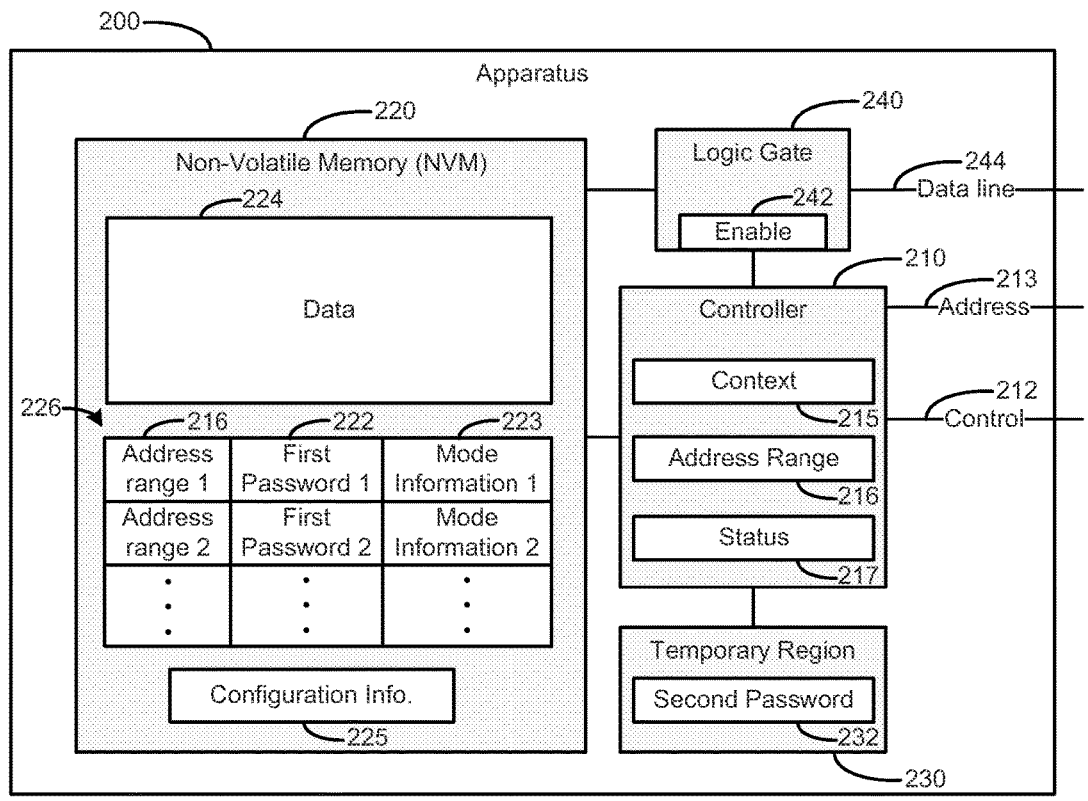
FIG. 2 is a block diagram of an apparatus including a table according to an example.

FIG. 2 is a block diagram of an apparatus 200 including a table 226 according to an example. Table 226 is contained in non-volatile memory (NVM) 220, which also includes data 224 and configuration info 225. The table 226 includes a plurality of address ranges 216, first passwords 222, and mode information 223. Apparatus 200 also includes controller 210, temporary region 230, and logic gate 240. The controller 210 is to receive address line 213 and control line 212, and includes context 214, address range 216 and status 217. The temporary region 230 includes a second password 232. The logic gate 240 is to receive data line 244, and includes enable 242.

Controller 210, including logic gate 240, may provide a control block interaction with address, data, and control signals (data line 244, address line 213, and control line 212) for interacting with apparatus 200 and its non-volatile memory (NVM) 220 array. Logic gate 240 may be based on a multiplexer (MUX) block under the control of the controller 210. Thus, the address 213, data 244, and control 212 signals may pass through the control block to enable in-band communication.

The table 226 of NVM 220 is associated with multiple address ranges 216. Each address range 216 may be associated with its own first password 222 and corresponding mode information 223. Accordingly, a plurality of contexts may be supported based on the table 226, enabling multiple users to access independently protected portions of the NVM 220. The controller 210 may map multiple address ranges 216, first passwords 222, and modes 223 together as a block, and switch contexts between them according to context 215 of the controller 210. Two 'rows' of information are specifically shown in table 226, and an arbitrary number of rows may be supported by table 226 depending on available resources.

Apparatus 200 may support various modes of operation, based on the ability to set various mode registers according to mode information 223, configuration information 225, context 215, and/or status 217. For example, mode/configuration information may determine whether the controller 210 is allowed to reset/zero-out the entire NVM 220 array, or selective portions (e.g., corresponding to a context 215 and row of table 226 for a user/password). Address range checking may be performed, including applying different password testing depending on the address associated with data that is presented. Different types of accesses (e.g., read and/or write) may be permitted based on the modes/configurations for the various access models.

The mode information 223 (e.g., stored as mode bits) or other status/configuration/context/address range information may reveal whether the apparatus 200 is in a reset mode/process or other mode. The apparatus 200 may be operated in a new password acceptable mode, where the apparatus 200 is unowned/unclaimed, such that the first password 222 is unwritten/unclaimed. Various additional modes may be supported, such as diagnostic modes, manufacturing modes, and so on.

Address range 216 information (e.g., range registers), and other information in NVM 220 such as mode information 223 and configuration information 225, may itself be protected or otherwise privileged from modification unless appropriate modification access has been granted. For example, an 'administrator' entry in table 226 may be used to grant access to administer such information (e.g., based on a 'master' password/key), including setup and modification of address ranges and modes for other users. Thus, although a user may have control over, e.g., his or her corresponding password and data, that user's address space/range registers and modes may be privileged from modification by that user without proper password authentication for such updating. In an example, users who do not have administrator/master key privileges may be prevented from modifying information parameters corresponding to other users. Thus, even if a user knows the first password 222 for his account, he may be prevented from interfering with his and/or other account parameters that enable partitioned functionality and data access controls. A user's first password 222 may be associated with administrative privileges, i.e., the administrator functionality may be combined with, and does not need to be provided separately from, a user account.

Address range checking may be provided based on a corresponding set of mode information 223 (e.g., mode bits) for each address range 216. Mode information 223 may be provided per each operational address range 216 (i.e., per row of table 226), because apparatus 200 may support the ability to independently reset each first password 222 without having to reset all first passwords 222 simultaneously. Thus, a first password 222 for one user may be set, without locking out other users from their respective access to NVM 220. Such functionality may enable the apparatus 200 to appear as multiple devices. Additionally, such multiple context 215 functionality enables the migration of specific address ranges (i.e., rows of table 226 and corresponding address ranges 216 of the data 224), without needing to migrate the entire contents of the NVM 220, although migrating the entire contents of apparatus 200 is also supported. Thus, examples of apparatus 200 support the case of migrating a given range corresponding to a particular user, processor, and/or node, as well as the case of migrating all data from a suspected dying apparatus 200 to a healthy replacement device.

Resources of apparatus 200 may be divided up to enable accessing corresponding contexts 215, e.g., sharing of resources among multiple users. Performing range checking enables the controller 210 to ensure that a given context (e.g., user) is allowed access to only the resources associated with that context. Thus, protected storage may be subdivided for sharing, while preserving individual protection on a per-user basis.

The controller 210 may use various techniques of recognizing which of various contexts 215 is requesting a given piece of data at any given time. In an example, two users are each using half the resources of apparatus 200 based on access only to their respective half of the device. Such usage may be accomplished based on two stored first passwords 222. The controller 210 may use address range checking to determine which password should be used to test access for a given request that has arrived at the controller 210. If the request is associated with an address range corresponding to the first user, then the request may be applied towards authenticating a first password 222 from that first user. A similar address range check may be applied for an arbitrary number of users.

The configuration information 225 may include a valid bit, or other flag/indicator in hardware that indicates that a write has occurred to the contents of the temporary region 230 (e.g., to the location of the second password 232). The valid indicator may indicate that the second password 232 has been validated, as stored in the configuration information 225. Various options are possible, including authenticating the second password 232 with each data interaction, or authenticating a fewer number of times and allowing access based on an indication that authentication has occurred previously. The particular authentication option(s) implemented may be based on a state machine associated with the apparatus 200 (see, e.g., FIG. 5 as an example state machine). The state machine may have an input that indicates whether password validation has occurred. That input may be registered and remain registered until a password is written differently. Or, the validation input may be expressed as the dynamic output of a comparator that checks password validation repeatedly and/or constantly. Such various implementations are contemplated based on the examples provided herein.

Figure 3:
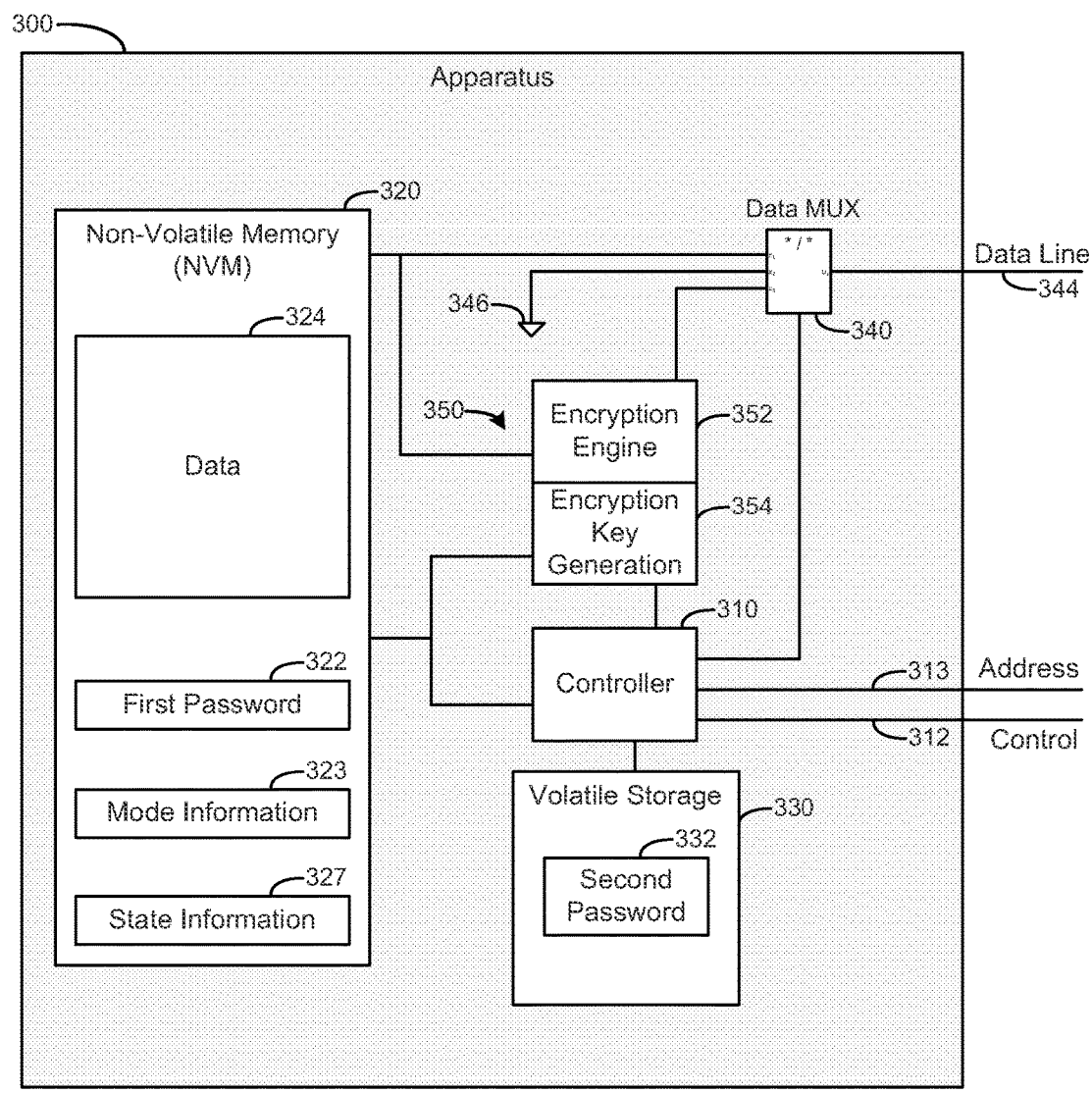
FIG. 3 is a block diagram of an apparatus including a cryptographic engine according to an example.

FIG. 3 is a block diagram of an apparatus 300 including a cryptographic engine 350 according to an example. The cryptographic engine 350 includes an encryption engine 352 and an encryption key generation 354. The apparatus 300 also includes non-volatile memory (NVM) 320, controller 310, volatile storage 330, and data multiplexor (MUX) 340. The NVM 320 includes data 324, first password 322, mode information 323, and state information 327. The controller 310 is to receive the address line 313 and control line 312. The volatile storage 330 includes second password 332. The data MUX 340 is to receive the data line 344.

As shown in FIG. 3, access to non-volatile memory (NVM) 320 may bypass the cryptographic engine 350 via the data multiplexer (MUX) 340 to data line 344. Thus, it is possible to interact with NVM 320 directly, without additional latency costs that may be introduced by cryptographic operations. For example, data 324 may be stored and retrieved in an unencrypted format, in examples where MUX 340 is set to bypass the cryptographic engine 350. However, if data 324 is stored in an encrypted format (e.g., using the cryptographic engine 350 during writing of data 324, or bypassing the cryptographic engine 350 to directly write already-encrypted data), the cryptographic engine 350 may be bypassed to read/retrieve that encrypted data 324, to maintain the cryptographic security of the data (e.g., to migrate the encrypted data without knowing the encryption password).

The cryptographic engine 350 may be implemented based on an industry standard encryption scheme, such as the Advanced Encryption Standard (AES) or other schemes. Although an encryption engine 352 is specifically labeled, the encryption engine 352 also may be used to perform decryption operations. Cryptographic operations may be applied via a sideband path, so that retrieving the data contents via the sideband path without an encryption key may result in data contents in an encrypted format (e.g., using a stored lock key as a symmetric encryption key). Encrypted data readout may be available through the main data path, e.g., after being enabled by selection of such a readout mode. Such techniques allow recovery of memory contents (e.g., by an unrelated administrator/technician) without knowing the key. The key holder may decrypt such recovered/migrated encrypted memory contents, which may be re-loaded to another system. Asymmetric keying also may be used. Such techniques enable migration of the data 324, and any other related information such as the first password(s) 322, mode information 323, state information 327, and other contents, to another device and another location, without compromising the security of such data/information. In an example, such migration may be carried out without needing to know the passwords, enabling a technician to migrate data without needing to obtain any information from the end user whose data remains protected during migration.

The cryptographic engine 350 may add an additional level of security, based on use of an encryption password (e.g., encryption key) separate from and in addition to the first password 322 and second password 332. Thus, even when bypassing the cryptographic engine 350, examples of apparatus 300 may enable data 324 to remain protected based on the selective gating/locking according to authentication of the first password 322. Such doubly protected data enables a higher overall data security compared to data protected by encryption alone, or the lock mechanism alone. The lock mechanism provided by authentication of first password 322 also may be applied as an extra layer of protection over the encryption protection provided by the cryptographic engine 350. The lock mechanism may resist concerted efforts to break an encryption key, by examining encrypted data and attempting to match the encrypted data to known patterns, because null data may be provided if the proper second password 332 is not provided to authenticate the first password 322. Although FIG. 3 shows one set of first/second passwords 322, 332, and other configuration data such as mode information 323 and state information 327, examples may use the multi-context features described above (e.g., based on table 226 of FIG. 2).

In an example, the cryptographic engine 350 may be operated in an 'encrypt-out' mode (e.g., as indicated by and according to mode information 323) to encrypt the data 324 when read out, (e.g., even if previously accessed unencrypted when not operating apparatus 300 in such a mode). Encrypting the data 324 when read out enables moving the encrypted data 324 to another similar apparatus 300, without incurring encryption latency during normal operation. Thus, the data 324 may be protected by the lock mechanism of authentication of first password 322 in other modes, and may be protected by both the lock mechanism and the encryption in the in the 'encrypt-out' mode. Thus, the cryptographic engine 350 may be selectively enabled and/or disabled based on the controller 310 and/or MUX 340, depending on mode information and desired level of protection vs. performance/latency, for example. Examples of apparatus 300 may include additional logic to achieve such flexibility.

Examples of apparatus 300 are therefore redeployable in, e.g., a data center where the hardware is being used and redeployed among different OSes. If there is a need to redeploy a particular piece of hardware that a user has run, the user's data may be moved to another system without a need to know the user's first password 322 and/or encryption key(s). The data 324 remains protected and inaccessible until migrated to a new system where user's first password 322 may be authenticated and/or the data 324 may be decrypted based on the user's encryption key(s). Thus, a user may move to a new system for better performance or other benefits, based on an administrator moving the data without revealing the contents of the data in any recognizable format. The data and other configuration information may be moved from one device/machine to another, with password protection along the way. Logic provided by controller 310, encryption engine 350, and/or MUX 340 enables encryption protection. The cryptography may run at a slower speed than real-time, enabling the use of resources having a lighter data/resource/latency footprint. The ability to move encrypted data without resetting the password(s) and without destroying the data provides additional usability and portability.

A benefit of approaching data protection in system memory using examples of apparatus 300 based on these dual mechanisms (lock and/or encryption), is that by using the password locking mechanism, data access may be faster (e.g., lower latency) compared to when using the encryption mechanism. It is possible to use the password/locking model on a day-to-day basis without encryption, and when occasionally migrating the data, then encryption may be used during those select/few times. In alternate examples, the password locking and encryption may be used simultaneously regardless of a particular scenario.

Accordingly, examples based on apparatus 300 may provide the benefit of reusability and migratability. Reusability is enabled by the ability to reset a lost password and guarantee that the data is zeroed out in the process of restoring the apparatus 300 to a reusable status. Encryption enables the ability to read out the data and related configuration information (including the first password 322), encrypt that data/information, and migrate it to a new device without a need to know the password(s), guaranteeing data security when moving to the new device.

Various specific techniques may be used to implement encryption. To migrate the data 324, encryption may use passwords/keys known to the migrator, without a need to know the first password 322. The migrator may supply the encrypted password. In alternate examples, asymmetric keying may be used. The cryptographic engine 350 (e.g., the encryption key generation 354) may contain a private key, which is associated with a corresponding public key. The private key may be built-in at manufacture, or may be generated.

Consider a source device (example apparatus 300) and a destination device (example apparatus 300), between which data 324 is to be migrated by an administrator. The destination device is known to the administrator, along with a public key corresponding to that destination device. That public key would be provided to the source device for encrypting its data. For example, the public key may be received at the source device via data line 344, along with a control signal 312 instructing the controller 310 that a public key is being received. The source device may use the received public key at the cryptographic engine 350 to encrypt the contents of NVM 320 (data 324, first password(s) 322, mode information 323, and/or state information 327, and so on). The contents may be encrypted as they are being read out, e.g., by putting the source device in encrypted mode readout. The source device may encrypt using both the public key of the destination device, and the first password 322 of the source device (which may be unknown to the administrator). Accordingly, the source device has a secret first password 322, and the destination device has a secret private key, that may be unknown to the administrator doing the migration, thereby ensuring that encrypted information is safe. In an alternate example, the migration process may result in unencrypted data at the destination device, so that when the migration process is complete, the destination device would be a clone of the source device. Thus, the destination device would be ready for use as though it were the source device, e.g., by authenticating the first password 322 at the destination device without a need to decrypt anything. In an alternate example, the migration process may result in encrypted data at the destination device, such that use of the destination device would involve enabling the device for decryption.

In an example, the cryptographic engine 350 may encrypt the contents of NVM 320 before they are read out, and may encrypt in a format that needs the first password 322 for decrypting. The data 324, and/or the entire contents of NVM 320, may be stored in an encrypted format that is unreadable until the second password 332 is provided to authenticate the first password 322, at which point the cryptographic engine 350 could run decryption to enable read out of the contents of NVM 320.

Figure 4:
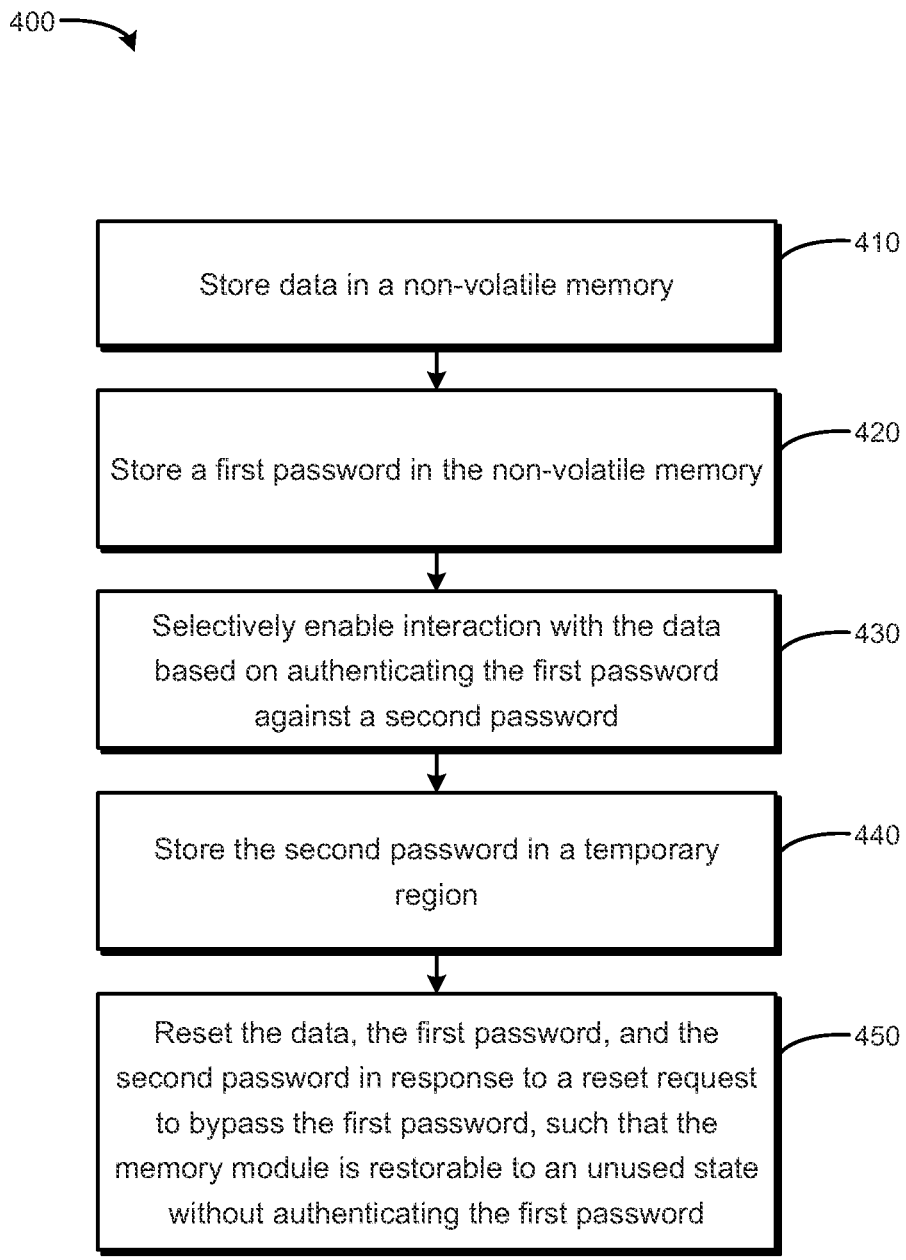
FIG. 4 is a flow chart based on storing data in a non-volatile memory according to an example.
Figure 5:
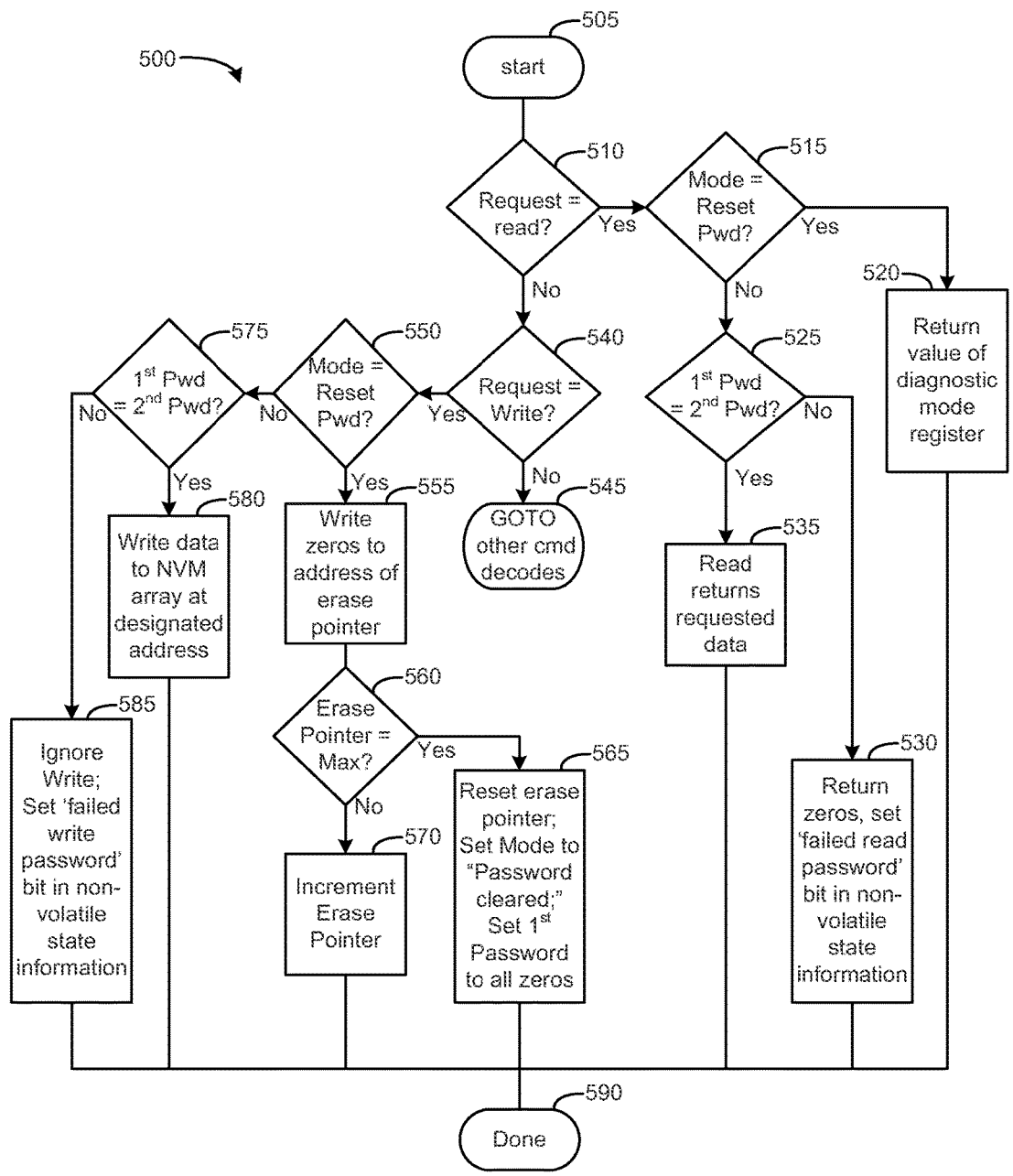
FIG. 5 is a flow chart based on interacting with a non-volatile memory according to an example.

Referring to FIGS. 4 and 5, flow diagrams are illustrated in accordance with various examples of the present disclosure. The flow diagrams represent processes that may be utilized in conjunction with various systems and devices as discussed with reference to the preceding figures. While illustrated in a particular order, the disclosure is not intended to be so limited. Rather, it is expressly contemplated that various processes may occur in different orders and/or simultaneously with other processes than those illustrated.

FIG. 4 is a flow chart 400 based on storing data in a non-volatile memory according to an example. In block 410, data is stored in a non-volatile memory (NVM). For example, an NVM memory module may be used as system memory in a computing system, storing random access data during operation of the computer. In block 420, a first password is stored in the NVM. For example, the NVM may be in an un-owned condition, operating according to a new password acceptable mode, where the NVM may be owned by writing the first password into the NVM. In block 430, interaction with the data is selectively enabled based on authenticating the first password against a second password. For example, a user may be denied interaction with the NVM that is protected by the first password, until the user enters a second password that is authenticated against the stored first password in the NVM, to grant interaction with the NVM. In block 440, the second password is stored in a temporary region. For example, an apparatus may include a volatile region that is to store the second password temporarily. In alternate examples, the second password may be stored in a non-volatile region that is caused to effectively behave as though it were temporary, e.g., by resetting (e.g., zeroing out) the non-volatile temporary region upon system reset or power up. In block 450, the data, the first password, and the second password are reset in response to a reset request to bypass the first password, such that the memory module is restorable to an unused state without authenticating the first password. For example, a memory module based on the examples herein, that was previously used in a first computing system, may be repurposed for use in a second computing system, without a need to know any passwords that were previously used to secure the memory module. The repurposed memory module may be made ready for a new user to take ownership by entering a new first password, all without needing to even know the earlier password.

FIG. 5 is a flow chart 500 based on interacting with a non-volatile memory according to an example. Flow chart 500 may represent an example state machine. Flow begins at block 505. In block 510, the system may check whether a read request is received. If yes, flow proceeds to block 515, where the system may check whether the mode is a reset password mode. If yes, flow proceeds to block 520, and a value of a diagnostic mode register is returned corresponding to a password reset. If in block 515 the mode is not reset password, flow proceeds to block 525, where it is determined whether the first password and the second password are equal. If not, flow proceeds to block 530, and the system is to return zeros, and set a 'failed read password' bit in the non-volatile state information. If in block 525 the first and second passwords are equal, flow proceeds to block 535, where the read is to return the requested data.

If in block 510 it is determined that the request is not a read, flow proceeds to block 540, where it is determined whether the request is a write. If not, flow proceeds to block 545, where flow may go to various other command decodes. If in block 540 it is determined that the request is a write, flow proceeds to block 550, where it is determined whether the mode is to reset the password. If yes, flow proceeds to block 555, in which the system writes zeros to the address of the erase pointer. In block 560, it is determined whether the erase pointer is at maximum. If yes, flow proceeds to block 565, in which the system resets the erase pointer, sets the mode 'password cleared,' and sets the first password to all zeros. If in block 560 it is determined that the erase pointer is not at maximum, flow proceeds to block 570, and the erase pointer is incremented. If in block 550 it was determined that the mode is not reset password, flow proceeds to block 575, where it is determined whether the first password and second password are equal. If equal, flow proceeds to block 580, in which the system writes data to the NVM array at the designated address. If at block 575 it is determined that the first and second passwords are not equal, flow proceeds to block 585, in which the system ignores the write, and sets a 'failed write password' bit in the non-volatile state information. Flow ends at block 590.

Examples provided herein may be implemented in hardware, software, or a combination of both. Example systems can include a processor and memory resources for executing instructions stored in a tangible non-transitory medium (e.g., volatile memory, non-volatile memory, and/or computer readable media). Non-transitory computer-readable medium can be tangible and have computer-readable instructions stored thereon that are executable by a processor to implement examples according to the present disclosure.

An example system (e.g., a computing device) can include and/or receive a tangible non-transitory computer-readable medium storing a set of computer-readable instructions (e.g., software). As used herein, the processor can include one or a plurality of processors such as in a parallel processing system. The memory can include memory addressable by the processor for execution of computer readable instructions. The computer readable medium can include volatile and/or non-volatile memory such as a random access memory ("RAM"), magnetic memory such as a hard disk, floppy disk, and/or tape memory, a solid state drive ("SSD"), flash memory, phase change memory, and so on.

What is claimed is:

1. An apparatus comprising:
 a non-volatile memory (NVM) to store data and a first password, wherein the first password is to protect the data;
 a controller to selectively enable interaction with the data based on authenticating the first password against a second password; and
 a region of the non-volatile memory having an address range allocated as non-persistent and behaving as a temporary region that is cleared responsive to any of a reset, power loss, or power cycle occurring, by zeroing out of the region, the temporary region to store the second password;
 wherein the data, the first password, and the second password are resettable by the controller in response to a reset request to bypass the first password, such that the apparatus is restorable to an unused state without authenticating the first password.

2. The apparatus of claim 1, wherein, in response to the reset request, the controller is to reset the data, the first password, and the second password based on writing zeros into writeable data locations, and the controller is to determine that all locations are zeroed prior to clearing the first password and rendering the apparatus in the unused state.

3. The apparatus of claim 1, further comprising an encryption engine to encrypt at least a portion of the data, wherein the controller enables bypassing the first password to retrieve encrypted data from, and load encrypted data to, the apparatus to migrate the encrypted data without authenticating the first password.

4. The apparatus of claim 3, wherein the encryption engine is to perform cryptographic operations based on a public key and private key pair, according to asymmetric keying to enable migration of the encrypted data between a source apparatus and a destination apparatus without compromising the private key.

5. The apparatus of claim 3, wherein the data is stored unencrypted at the apparatus, and the encryption engine is to encrypt at least a portion of the data according to the encryption password in response to a request to migrate the data, according to an encrypted mode readout to encrypt as data is being read out.

6. The apparatus of claim 3, wherein the apparatus is to decrypt the encrypted data based on the private key and authenticating the first password.

7. The apparatus of claim 1, wherein the controller is to enable interaction with the data according to mode information stored in the NVM, wherein the mode information is to indicate a mode of operation of the apparatus including a reset mode.

8. The apparatus of claim 1, wherein the controller is to apply address range checking to a received address signal, wherein an address range and associated mode information correspond to the first password, wherein the controller is to support a plurality of address ranges and corresponding mode information, isolated by corresponding passwords.

9. The apparatus of claim 8, wherein the address range and associated mode information corresponding to the first password are protected against modification based on authentication of a master password.

10. The apparatus of claim 8, wherein the apparatus is to migrate data corresponding to the address range, without migrating remaining portions of the data corresponding to a remaining plurality of address ranges.

11. The apparatus of claim 10, wherein the apparatus includes an interface to serve as system memory of a computing system.

12. An apparatus comprising:
 a non-volatile memory (NVM) to store data and a first password;
 a controller to selectively enable interaction with the data based on authenticating the first password against a second password; and
 a region of the non-volatile memory having an address range allocated as non-persistent and behaving as a temporary region that is cleared responsive to any of a reset, power loss, or power cycle occurring, by zeroing out of the region, the temporary region store the second password
 wherein the data and the first password of the non-volatile memory are resettable by the controller in response to a reset request to bypass the first password, such that the memory module is restorable to an unused state without authenticating the first password.

13. A method, comprising:

storing data in a non-volatile memory;

storing a first password in the non-volatile memory;

selectively enabling interaction with the data based on authenticating the first password against a second password;

storing the second password in a region of the non-volatile memory having an address range allocated as non-persistent and behaving as a temporary region that is cleared responsive to any of a reset, power loss, or power cycle occurring, by zeroing out of the region;

responsive to the reset, power loss, or power cycle occurring, discarding the second password from the temporary region by zeroing out the region; and resetting the data, the first password, and the second password in response to a reset request to bypass the first password, such that the memory module is restorable to an unused state without authenticating the first password.

14. The method of claim 13, further comprising:

encrypting the data; and bypassing the authenticating the first password to migrate the encrypted data from the non-volatile memory.

* * * * *